(12) United States Patent
O'Bryan et al.

(10) Patent No.: US 12,285,574 B2
(45) Date of Patent: Apr. 29, 2025

(54) ERGONOMIC IV SYSTEMS AND METHODS

(71) Applicant: Becton, Dickinson and Company, Franklin Lakes, NJ (US)

(72) Inventors: Jeffrey C. O'Bryan, Murray, UT (US); Gary Shearer, Phoenix, MD (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 329 days.

(21) Appl. No.: 17/874,574

(22) Filed: Jul. 27, 2022

(65) Prior Publication Data
US 2022/0362521 A1 Nov. 17, 2022

Related U.S. Application Data

(60) Continuation of application No. 16/838,812, filed on Apr. 2, 2020, now Pat. No. 11,426,558, which is a division of application No. 15/461,358, filed on Mar. 16, 2017, now Pat. No. 10,639,454.

(60) Provisional application No. 62/314,260, filed on Mar. 28, 2016.

(51) Int. Cl.
*A61M 25/06* (2006.01)
*A61M 5/158* (2006.01)
*A61M 25/00* (2006.01)

(52) U.S. Cl.
CPC ........ *A61M 25/0606* (2013.01); *A61M 5/158* (2013.01); *A61M 25/0631* (2013.01); *A61M 25/0097* (2013.01); *A61M 25/0637* (2013.01); *A61M 2205/586* (2013.01)

(58) Field of Classification Search
CPC ........ A61M 2205/586; A61M 25/0097; A61M 25/0631; A61M 25/0637; A61M 5/158; A61M 25/06
See application file for complete search history.

(56) References Cited

U.S. PATENT DOCUMENTS

| | | | |
|---|---|---|---|
| 4,311,137 A | 1/1982 | Gerard | |
| 5,554,127 A | 9/1996 | Crouther et al. | |
| 5,676,656 A | 10/1997 | Brimhall | |
| 6,786,875 B2 * | 9/2004 | Barker | A61B 5/1535 604/164.12 |

(Continued)

FOREIGN PATENT DOCUMENTS

| | | |
|---|---|---|
| CA | 2422307 A1 | 9/2003 |
| CN | 101879341 A | 11/2010 |

(Continued)

*Primary Examiner* — Deanna K Hall
(74) *Attorney, Agent, or Firm* — Kirton McConkie; Whitney Blair; Kevin Stinger

(57) ABSTRACT

An IV catheter system may include a catheter component with a catheter hub, a cannula extending distally from the catheter hub, and a securement platform. The securement platform may include a wing, which may extend from the catheter hub. The IV catheter system may also include a needle component with a needle hub, a needle extending distally from the needle hub along an axis, and a grip extending from the needle hub. The grip may be generally parallel to the axis and disposed on a side of the needle hub. The wing and the grip may be positioned to facilitate manipulation with a single hand to move the IV catheter system from an insertion configuration towards a fluid delivery configuration.

5 Claims, 11 Drawing Sheets

(56) References Cited

U.S. PATENT DOCUMENTS

| | | |
|---|---|---|
| 7,294,118 B2 | 11/2007 | Saulenas et al. |
| 8,337,461 B2 | 12/2012 | Burkhloz |
| 8,357,121 B2 | 1/2013 | Burkhloz |
| 2001/0041871 A1 | 11/2001 | Brimhall |
| 2003/0078540 A1 | 4/2003 | Saulenas et al. |
| 2003/0220619 A1 | 11/2003 | Polidoro et al. |
| 2007/0270758 A1 | 11/2007 | Hanner et al. |
| 2010/0249713 A1 | 9/2010 | Burkholz |
| 2011/0009717 A1 | 1/2011 | Davis et al. |
| 2012/0220945 A1 | 8/2012 | Rizzo et al. |

FOREIGN PATENT DOCUMENTS

| | | | |
|---|---|---|---|
| CN | 102413865 A | 4/2012 |
| CN | 102716541 A | 10/2012 |
| CN | 202909200 U | 5/2013 |
| CN | 103301528 A | 9/2013 |
| CN | 205019559 U | 2/2016 |
| EP | 0732120 A1 | 9/1996 |
| EP | 0796117 A1 | 9/1997 |
| EP | 2077133 A1 | 7/2009 |
| EP | 2272432 A1 | 1/2011 |
| JP | 6025166 A | 2/2000 |
| JP | 2003180829 A | 7/2003 |
| JP | 5025166 B2 | 9/2012 |
| JP | 2012521797 A | 9/2012 |
| WO | 8807388 A1 | 10/1988 |
| WO | 0545671 A1 | 6/1993 |
| WO | 9842393 A1 | 10/1998 |
| WO | 0012171 A1 | 3/2000 |
| WO | 2008000148 A1 | 1/2008 |
| WO | 2009129290 A1 | 10/2009 |
| WO | 2010111285 A1 | 9/2010 |
| WO | 2011109542 A1 | 9/2011 |
| WO | 2014201709 A1 | 12/2014 |
| WO | 2015118109 A1 | 8/2015 |
| WO | 2016007442 A1 | 1/2016 |

\* cited by examiner

ERGONOMIC IV SYSTEMS AND METHODS

RELATED APPLICATIONS

This application is a continuation of U.S. patent application Ser. No. 16/838,812, filed on Apr. 2, 2020, entitled ERGONOMIC IV SYSTEMS AND METHODS, which is a divisional of U.S. patent application Ser. No. 15/461,358, filed on Mar. 16, 2017, entitled ERGONOMIC IV SYSTEMS AND METHODS, which claims the benefit of U.S. Provisional Patent Application Ser. No. 62/314,260, filed on Mar. 28, 2016, and entitled ERGONOMIC IV SYSTEMS AND METHODS, which are incorporated herein in their entirety.

BACKGROUND

The present invention is generally directed to systems and methods for intravenous ("IV") delivery, by which fluids can be administered directly to the vascular system of a patient. More particularly, the present invention is directed to IV catheter systems and methods that facilitate insertion into the patient and/or motion from an insertion configuration to a fluid delivery configuration in which fluid can be delivered to the patient through the IV catheter system. An IV catheter system according to the invention is used broadly herein to describe components used to deliver the fluid to the patient, for use in arterial, intravenous, intravascular, peritoneal, and/or non-vascular administration of fluid. Of course, one of skill in the art may use an IV catheter system to administer fluids to other locations within a patient's body.

Known IV catheter systems and methods have a number of deficiencies. Many such systems require the clinician to use two hands to position the IV catheter system and/or insert the needle into the fluid delivery location on the patient (for example, the vein into which fluid is to be delivered). Further, many such systems require the clinician to use two hands to move the IV catheter system from the insertion configuration to a fluid delivery configuration, in which the needle is removed from the cannula to permit fluid to be delivered to the vein through the cannula. Thus, the clinician is required to stabilize the patient's arm or other body part having the fluid delivery location prior to insertion of the IV catheter system. As a result, extra time is required for the clinician to initiate transfusion. Further, the clinician is unable to perform any other task, such as stabilizing or reassuring the patient, during insertion and/or motion to the fluid delivery configuration.

Accordingly, there is a need for IV catheter systems and methods that facilitate IV catheter system placement, insertion, and/or preparation for fluid delivery. There is a further need for such IV catheter systems that are inexpensive, easy to manufacture, and versatile.

BRIEF SUMMARY OF THE INVENTION

Embodiments of the present invention are generally directed to an IV catheter system with enhanced ergonomics. In some embodiments, the IV catheter system may be inserted and moved toward the fluid delivery configuration with only one hand. Moving the IV catheter system toward the fluid delivery configuration may facilitate "hooding" of the needle. In some instances, a diameter of a targeted vein may be relatively small compared to a gauge of the needle. Thus, it is not uncommon for a beveled portion of the needle to breach or otherwise damage the vein while advancing the cannula and the needle into the vein. Accordingly, it is a common practice to "hood" the needle once the vein has been accessed via the needle and tip of the cannula.

A process of hooding the needle involves maintaining a stationary position of the partially inserted cannula while simultaneously withdrawing the beveled portion of the needle into the inner lumen of the cannula. Once the needle has been hooded, the cannula may be advanced into the vein to a desired position. With the needle hooded, there may be no danger of damaging the vein while advancing the cannula. In some instances, when the needle is hooded, the beveled portion may be withdrawn into the inner lumen of the cannula such that the beveled portion is at least proximate the tip of the cannula. Thus, the needle extending through the cannula and at least proximate the tip of the cannula may provide increased rigidity as the cannula is advanced into the vein.

In some embodiments, the securement platform may be positioned to receive first contact from the first digit of the hand of the user to urge the catheter hub distally. The first digit of the hand may include, for example, a thumb of the user. In some embodiments, the grip of the needle component may be positioned to receive second contact from the second digit of the hand simultaneously with receipt of the first contact such that the first and second contacts cooperate to move the IV catheter system from the insertion configuration toward the fluid delivery configuration. The second digit may include, for example, an index finger of the user.

In some embodiments, the grip may include an upper surface. In some embodiments, the upper surface of the grip may receive the second contact. In some embodiments, when the IV catheter system is in the insertion configuration, the upper surface of the grip may be coplanar with an upper surface of a particular wing of the securement platform. In some embodiments, a distal end of the grip may contact a proximal end of the particular wing when the IV catheter system is in the insertion configuration. The upper surface of the particular wing may receive the first contact.

In some embodiments, the grip may include a support surface. In some embodiments, when the IV catheter system is in the insertion configuration, at least a portion of a bottom surface of the particular wing may contact the support surface. In some embodiments, the grip may include a stop surface, which may separate the upper surface of the grip and the support surface. In some embodiments, when the IV catheter system is in the insertion configuration, the proximal end of the particular wing may contact the stop surface. In some embodiments, during motion of the IV catheter system from the insertion configuration toward the fluid delivery configuration, at least a portion of the bottom surface of the particular wing may slide along the support surface.

In some embodiments, the grip may be disposed on a side of the needle hub. In some embodiments, the needle hub may include at least one gripping protrusion, which may be disposed proximal to the grip. In some embodiments, a particular gripping protrusion may be disposed on an opposite side of the needle hub as the grip. In some embodiments, the particular gripping protrusion may be positioned to receive third contact from a third digit of the hand of the user. The third digit may include, for example, a middle or ring finger of the user.

In some embodiments, once the IV catheter system is moved toward the fluid delivery configuration to hood the needle and the cannula is advanced to the desired position, an actuator button may be depressed to move the needle into the needle hub such that the needle is entirely enclosed within the needle hub in the fluid delivery configuration. In some embodiments, the actuator button may be disposed on a top portion of the needle hub, which may facilitate easy access of the actuator button and prevent blocking of the actuator button by the first digit and/or the second digit. In some embodiments, where the IV catheter system includes the first wing and the second wing, the actuator button may be disposed between the first wing and the second wing.

The IV catheter system may include any catheter system that includes a needle retractable into a needle hub. For example, in some embodiments, the IV catheter system may include the AUTOGUARD™ shielded catheter commercially available from Becton, Dickinson, and Company. In some embodiments, the IV catheter system may include any catheter system that includes a needle movable from a first position when the IV catheter system is in the insertion configuration, to a second position when the needle is hooded and the IV catheter system is transitioning from the insertion configuration to the fluid delivery configuration, and to a third, retracted or enclosed position when the IV catheter system is in the fluid delivery configuration.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
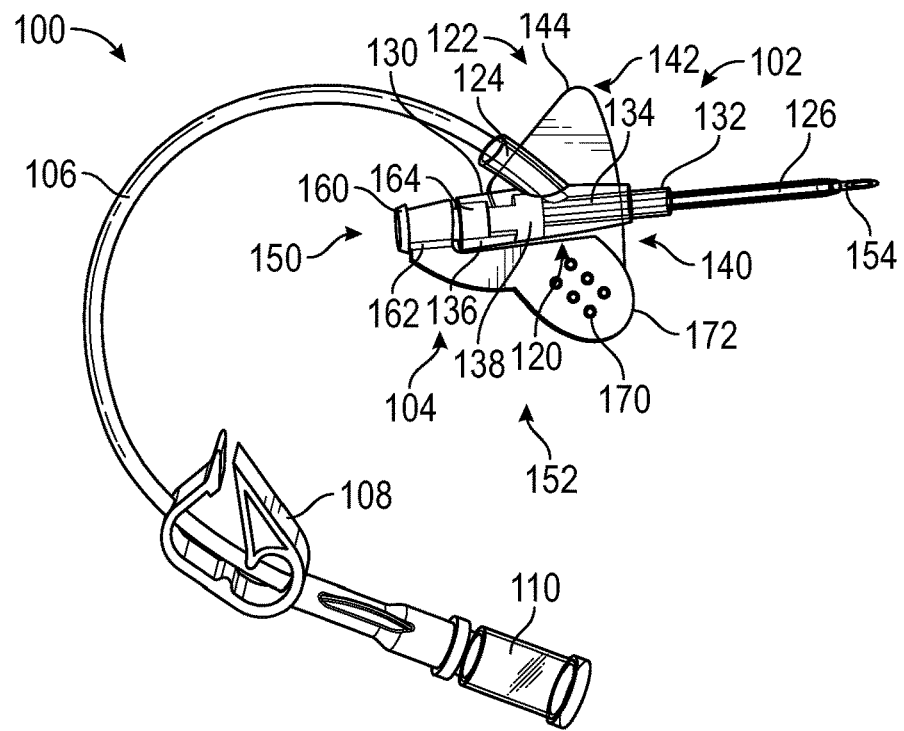
FIG. 1 is a perspective view of an IV catheter system according to one embodiment.

FIG. 1 is a perspective view of an IV catheter system 100 according to one embodiment. The IV catheter system 100 may be connected to a supply of fluid to be infused. The fluid supply (not shown) may include a bag of blood or medication to be delivered to the patient, a drip chamber that regulates flow of the fluid to the IV catheter system 100, and/or other components involved with the supply of fluid to the IV catheter system 100. The IV catheter system 100 may have a number of components, as shown in the exemplary embodiment of FIG. 1. These components may include a catheter component 102, a needle component 104, an extension tube 106, a clamp 108, and/or a luer lock adapter 110.

The catheter component 102 may be inserted into the fluid delivery location in the patient in order to convey the fluid to the patient. The needle component 104 may facilitate insertion of the catheter component 102 to the fluid delivery location. The extension tube 106 may convey the fluid to the catheter component 102. The clamp 108 may be used to manually block fluid flow to the catheter component 102 when it is desired to stop or pause fluid delivery. The luer lock adapter 110 may be readily connected to the fluid supply, for example, via connection to a complementary luer lock (not shown) of the fluid supply.

As embodied in FIG. 1, the IV catheter system 100 may be an integrated IV catheter system, as the extension tube 106 is pre-attached to the catheter component 102. In other embodiments, IV catheter systems of various open, integrated, and/or safety integrated configurations may be used.

The catheter component 102 may have various components, which may include a catheter hub 120, a securement platform 122, an extension tubing junction 124, and a cannula 126. The catheter hub 120 may have a generally tubular and/or hollow conical configuration, and may have a proximal end 130 and a distal end 132. The catheter hub 120 may be shaped to define a chamber 134 through which the fluid flows to reach the fluid delivery location. The catheter hub 120 may have a needle port 136 at the proximal end 130. The chamber 134 may contain a septum 138 that is designed to block flow of blood and/or the fluid to be delivered from the chamber 134 through the needle port 136. The cannula 126 may be secured to the distal end 132 of the catheter hub 120.

The securement platform 122 may have a generally planar configuration designed to permit the securement platform 122 to be secured to the skin of the patient, proximate the fluid delivery location, to keep the catheter component 102 securely in place as fluid delivery takes place. As embodied in FIG. 1, the securement platform 122 may have a first wing 140 with a generally planar shape, and a second wing 142 that also has a generally planar shape generally coplanar with the first wing 140. The second wing 142 may be positioned on the opposite side of the catheter hub 120 from the first wing 140. Thus, relative to the catheter hub 120, the first wing 140 and the second wing 142 may extend outward in opposite directions from the catheter hub 120. The first wing 140 and the second wing 142 may both be fixedly secured to the catheter hub 120, and may each have a generally triangular shape when viewed from along a direction perpendicular to the securement platform 122. In the alternative, the first wing 140 and/or the second wing 142 may have any shape, including but not limited to polygonal shapes such as triangular and rectangular shapes, and non-polygonal shapes such as circular, semicircular, oval, oblong, and irregular shapes. Some examples of these alternative shapes will be shown in subsequent embodiments. The first wing 140 and the second wing 142 may each have a trailing edge 144 oriented toward the proximal end 130 of the catheter hub 120.

The needle component 104 may have a needle hub 150, a grip 152, and a needle 154. The needle hub 150 may be detachably coupled to the catheter hub 120 of the catheter component 102. The grip 152 may extend outward from the needle hub 150. The needle 154 may be removably positioned within the cannula 126 such that the needle 154 facilitates the process of accessing the fluid delivery location (for example, a vein) and proper positioning of the cannula 126 to deliver the fluid to the fluid delivery location.

The needle hub 150 may have a generally tubular shape with a proximal end 160 and a distal end 162. The needle hub 150 may have a boss 164 positioned at the distal end 162; the boss 164 may be insertable into the needle port 136 of the catheter hub 120 of the catheter component 102.

The grip 152 may have a generally planar shape that extends outward from the needle hub 150. When viewed from a direction perpendicular to the grip 152, the grip 152 may have an oblong and/or partially elliptical shape. The grip 152, the first wing 140, and/or the second wing 142 may have one or more grip features 170, as shown on the grip 252, which may help provide a secure interface that facilitates gripping and/or moving the grip 152 by hand. The grip 152 may have a leading edge 172.

The IV catheter system 100 may have an insertion configuration, in which the IV catheter system 100 is readily insertable to position the cannula 126 in the fluid delivery location, and a fluid delivery configuration, in which the fluid flow through the cannula 126 is relatively unimpeded. In FIG. 1, the IV catheter system 100 is in the insertion configuration. The needle 154 is positioned within the cannula 126 to provide a sharpened tip for penetrating tissue and a relatively stiff body that supports the cannula 126 during insertion. The boss 164 of the needle hub 150 is positioned within the needle port 136 of the catheter hub 120. The needle 154 passes through the septum 138 of the catheter component 102.

The IV catheter system 100 may be inserted into position by positioning the tip of the cannula 126 proximate the fluid delivery location (for example, the patient's vein). The securement platform 122 may be placed on the patient's skin, proximate the fluid delivery location and/or held in the clinician's hand. The catheter component 102 and the needle component 104 may be advanced to push the cannula 126 until the tip of the cannula 126 penetrates the surrounding tissue and reaches the fluid delivery location. If desired, the catheter component 102 may be advanced by pushing a push surface of the catheter component 102. The "push surface" is a surface that is generally proximally-oriented, and thus can receive contact from the clinician's hand to urge the catheter component 102 and the needle component 104, together, distally.

Once the tip of the cannula 126 has reached the fluid delivery location, the IV catheter system 100 may be moved to the fluid delivery configuration. This may be done by withdrawing the needle component 104 proximally from the catheter component 102. This may initially cause the boss 164 to be withdrawn proximally from within the needle port 136. The needle 154 may also be withdrawn proximally from the cannula 126, and then through the chamber 134, including the septum 138. The needle 154 may pass out of the chamber 134 through the needle port 136, thus completing motion of the IV catheter system 100 to the fluid delivery configuration. Fluid flow to the fluid delivery location may now be accomplished by urging the fluid to flow through the extension tube 106, into the chamber 134, and through the cannula 126 to the fluid delivery location.

The IV catheter system 100 may advantageously be designed to facilitate insertion to the fluid delivery location to be readily performed with a single hand. For example, during insertion, the clinician may, with one hand, hold the catheter component 102 and the needle component 104, for example, by grasping the securement platform 122 and the grip 152. The clinician may then, with the same hand, apply gentle pressure to one or more push surfaces of the catheter component 102 (for example, the trailing edges 144 of the first wing 140 and/or the second wing 142) to urge the tip of the cannula 126 to penetrate the patient's skin and ultimately reach the fluid delivery location. If desired, one or more locking features (not shown) may be used to hold the catheter component 102 and the needle component 104 together until the clinician applies a threshold force to move the IV catheter system 100 from the insertion configuration to the fluid delivery configuration. Such locking features may take the form of interlocking features (not shown) between the boss 164 and the needle port 136, and/or the like.

The IV catheter system 100 may be designed to provide visual confirmation of proper placement in a blood vessel. For example, at least a portion of the catheter hub 120 may be translucent to provide visibility into the chamber 134. Thus, when the tip of the cannula 126 enters a vein, the resulting blood flow, or "flash," may be visible through the exterior wall of the catheter hub 120 as the blood enters the chamber 134. The extension tubing junction 124 and the extension tube 106 may also, optionally, be translucent. In some embodiments, the flash may extend through the extension tube 106 to the luer lock adapter 110. The luer lock adapter 110 may be coupled to the fluid supply in a manner that substantially prevents blood leakage.

Further, the IV catheter system 100 may advantageously be designed to facilitate motion from the insertion configuration to the fluid delivery configuration with a single hand. For example, the clinician may, with a single hand, which may be the same hand used to insert the IV catheter system 100 into the fluid delivery location, grasp the catheter component 102 and the needle component 104 and withdraw the needle component 104 proximally from the catheter component 102. The catheter component 102 may be left substantially in place so that only the needle component 104 moves significantly to move the IV catheter system 100 from the insertion configuration to the fluid delivery configuration.

This may be done by placing digits of the hand to contact the pull surface(s) of the needle component 104 and the push surface(s) of the catheter component 102, and then with those digits, pulling the needle component 104 proximally while pushing the catheter component 102 distally to keep it from moving proximally with the needle component 104. For example, the trailing edges 144 of the securement platform 122 may act as push surfaces, while the edge 172 of the grip 152 may act as a pull surface. The clinician may place one or more fingers on the leading edge 172 of the grip 152 and pulling proximally, while pushing with a thumb and/or one or more other fingers on the trailing edges 144 of the securement platform 122. Thus, the catheter component 102 may be kept in place with the tip of the cannula 126 at the fluid delivery location while the needle component 104 is withdrawn proximally from the catheter component 102 to unblock the fluid delivery path to the fluid delivery location.

The relative positions of the pull and push surfaces may facilitate single-handed operation in the manner described above. If desired, the coupling of the needle hub 150 with the catheter hub 120 may be such that the needle hub 150 is rotatable relative to the catheter hub 120 while the IV catheter system 100 is in the insertion configuration. Thus, the clinician may, with the hand, rotate the grip 152 to an orientation that is most comfortable for pulling on the leading edge 172, prior to pulling on the leading edge 172 and pushing on the trailing edges 144.

The septum 138 may have a "low friction" or "low drag" design configured to provide relatively low resistance to withdrawal of the needle 154 proximally through the septum 138, which occurs as the IV catheter system 100 transitions from the insertion configuration to the fluid delivery configuration. The resistance to withdrawal of the needle 154 through the septum 138 may be sufficiently low that the clinician can relatively easily move the IV catheter system 100 from the insertion configuration to the fluid delivery configuration with only a single hand. In some embodiments, the resistance to withdrawal may be, on average, less than about 50 gf.

Figure 2:
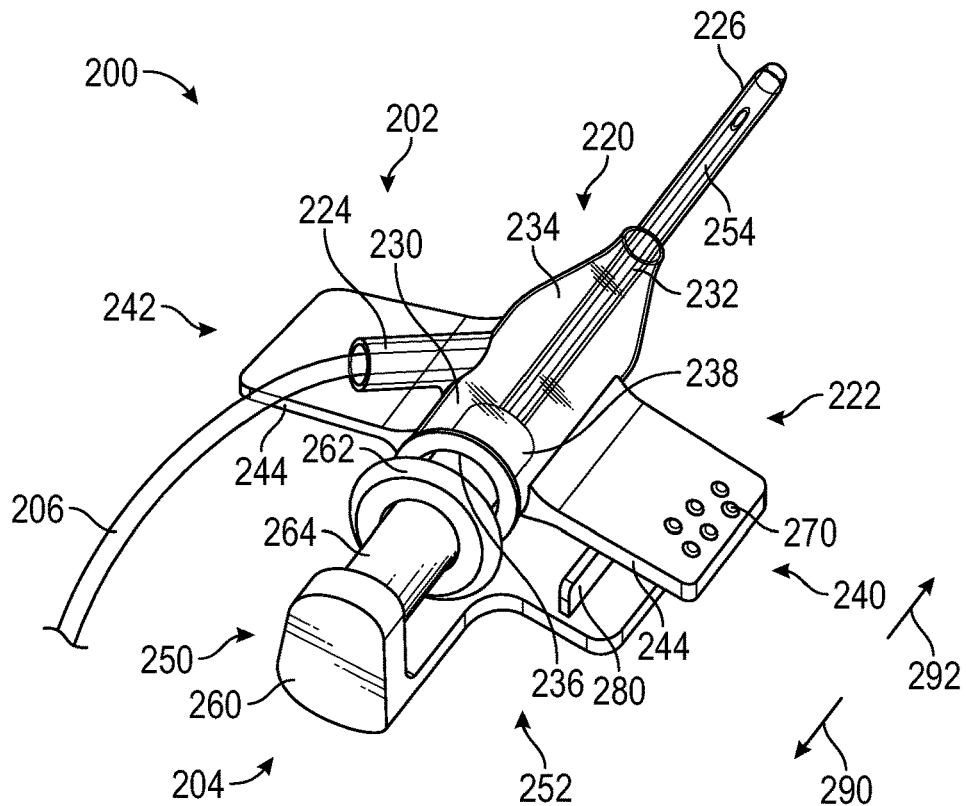
FIG. 2 is a perspective view of a portion of an IV catheter system according to one alternative embodiment.

FIG. 2 is a perspective view of a portion of an IV catheter system 200 according to one alternative embodiment. The IV catheter system 200 may have components that generally correspond to those of the IV catheter system 100 of FIG. 1. FIG. 2 illustrates only a catheter component 202, a needle component 204, and the distal end of an extension tube 206 connected to the catheter component 202. The IV catheter system 200 may have a configuration similar to that of the IV catheter system 100 of FIG. 1; however, some components may be shaped differently to provide alternative ergonomics.

The catheter component 202 may have a catheter hub 220, a securement platform 222, an extension tubing junction 224, and a cannula 226. The catheter hub 220 may have a generally tubular and/or hollow conical shape, with a proximal end 230 and a distal end 232. The catheter hub 220 may have a generally translucent exterior wall shaped to define a chamber 234 through which fluid flows to reach the fluid delivery location through the cannula 226. The catheter hub 220 may have a needle port 236 that connects to the needle component 204, proximate the proximal end 230 of the catheter hub 220. The catheter hub 220 may also have a septum 238 positioned within the chamber 234. The septum 238 may be a "low drag" septum as described previously.

The securement platform 222 may be attached to the skin of the patient during fluid delivery to keep the cannula 226 in place at the fluid delivery location. The securement platform 222 may have a first wing 240 and a second wing 242, which may both be generally planar in shape, and may extend in opposite directions relative to the catheter hub 220. Each of the first wing 240 and the second wing 242 may have a generally rectangular shape when viewed from perpendicular to the securement platform 222, with a trailing edge 244 that can act as a push surface.

The needle component 204 may have a needle hub 250, a grip 252, and a needle 254. The needle hub 250 may have a generally cylindrical shape with a proximal end 260 and a distal end 262. The needle hub 250 may also have a boss 264 that protrudes from the distal end 262 to interface with the needle port 236 of the catheter hub 220.

The grip 252 may have a generally planar shape, with a generally rectangular shape when viewed from perpendicular to the grip 252. The grip 252 may have a leading edge (not visible), which may serve as a pull surface. The grip 252, the first wing 240, and/or the second wing 242 may have one or more grip features 270, which may help provide a secure interface that facilitates gripping and/or moving the grip 152 by hand.

To move the IV catheter system 200 from the insertion configuration to the fluid delivery configuration, the clinician may position a digit (for example, a finger) on the leading edge of the grip 252, and a digit (for example, a finger or thumb) on the trailing edge 244 of the first wing 240 and/or the second wing 242. The clinician may then pull the leading edge proximally, as indicated by the arrow 290, and may push the trailing edge 244 of the first wing 240 and/or the second wing 242 distally, as indicated by the arrow 292. This may cause the catheter component 202 to remain in place while the needle component 204 is withdrawn proximally from the catheter component 202.

The grip 252 and the first wing 240 may be positioned parallel to each other, and may be positioned in close proximity to each other such that they are in abutting relation to each other in the insertion configuration, and during the initial stages of motion from the insertion configuration to the fluid delivery configuration. In order to maintain the desired relative positioning between the grip 252 and the first wing 240, the grip 252 and/or the first wing 240 may have one or more alignment features that maintain relative positioning and/or orientation between the first wing 240 and the grip 252.

Specifically, the grip 252 may have an alignment feature in the form of an alignment ridge 280, which may protrude toward the first wing 240, and may be received in a complementary alignment feature (not shown) such as a trough or other feature on the surface of the first wing 240 that faces toward the grip 252. The alignment ridge 280 and the complementary alignment feature may help keep the needle 254 parallel to the cannula 226 during motion of the IV catheter system 200 to the fluid delivery configuration. This may help ensure that the needle component 204 can be smoothly withdrawn from the catheter component 202. More specifically, application of imbalanced force on the catheter component 202 and/or the needle component 204 may urge the needle component 204 to rotate relative to the catheter component 202. For example, if the clinician is pulling on the leading edge of the grip 252 while pushing on the trailing edge 244 of the first wing 240, this may urge the needle component 204 to rotate clockwise, relative to the view of FIG. 2, with respect to the catheter component 202.

The alignment ridge 280 and the complementary alignment feature of the first wing 240 may help ensure that such relative rotation does not occur until the needle component 204 has been withdrawn from the catheter component 202 sufficiently to detach the alignment ridge 280 from the complementary alignment feature of the first wing 240. Thus, binding and/or other undesired interactions between the catheter component 202 and the needle component 204 may be avoided during motion from the insertion configuration to the fluid delivery configuration. Other examples of IV catheter systems according to various embodiments are described in U.S. Provisional Patent Application Ser. No. 62/296,385, filed Feb. 17, 2016, now U.S. application Ser. No. 15/286,168, filed Oct. 5, 2016 and which are incorporated herein.

Figure 3A:
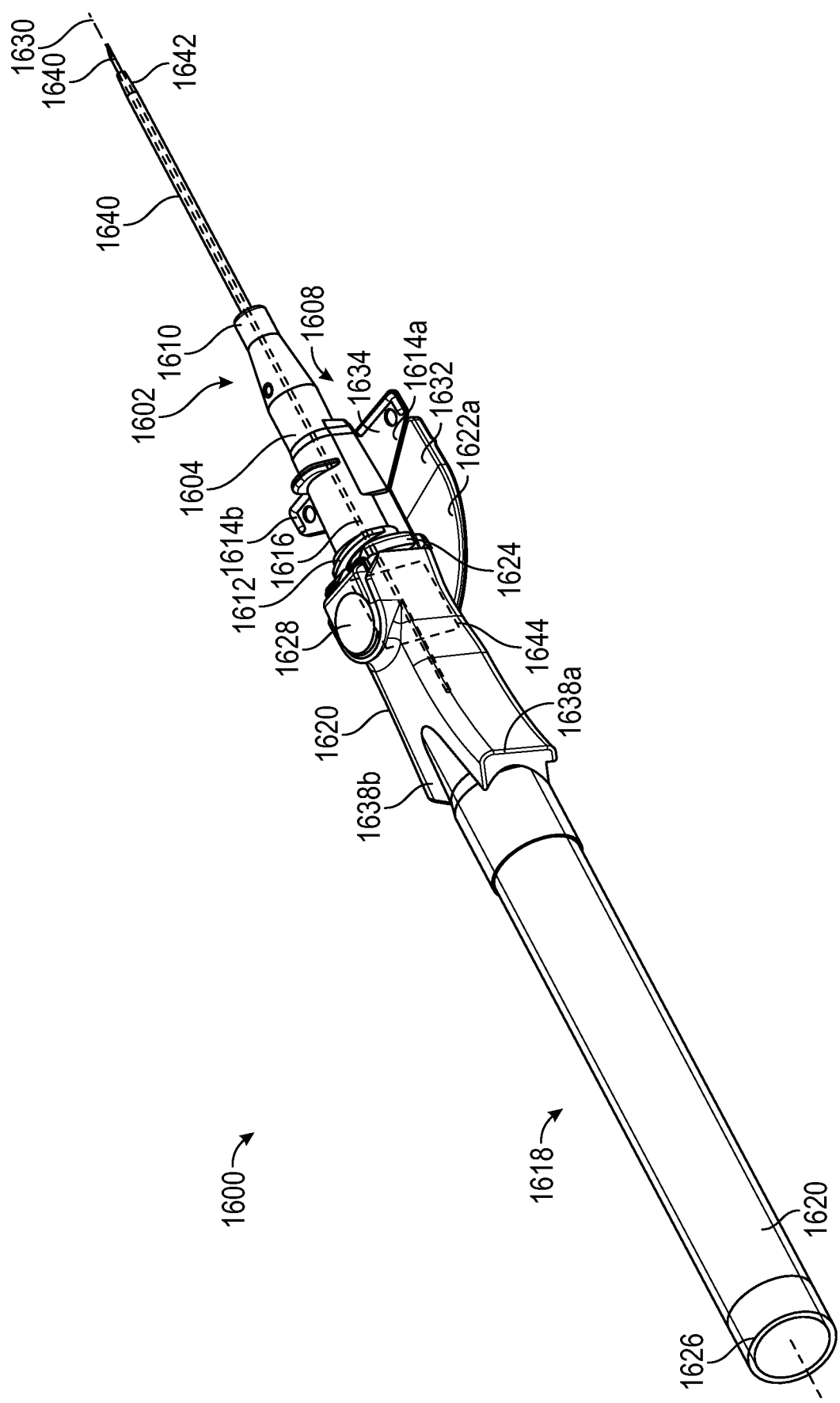
FIG. 3A is a perspective view of an IV catheter system according to yet another embodiment, illustrating the IV catheter system in the insertion configuration.

FIG. 3A is a perspective view of an IV catheter system 1600, according to some embodiments. In some embodiments, the IV catheter system 1600 may include an insertion configuration, illustrated in FIG. 3A. In some embodiments, the IV catheter system 1600 may include a catheter component 1602, which may include one or more of the following: a catheter hub 1604, a cannula 1606, and a securement platform 1608. In some embodiments, the catheter hub 1604 may include a distal end 1610 and a proximal end 1612. In some embodiments, the catheter hub 1604 may include a needle port disposed at the proximal end 1612 of the catheter hub 1604, through which a needle 1616 may extend. In some embodiments, the cannula 1606 may extend distally from the distal end 1610 of the catheter hub 1604. In some embodiments, the securement platform 1608 may include a first wing 1614a and/or a second wing 1614b, which may extend outwardly from the catheter hub 1604.

In some embodiments, the IV catheter system 1600 may include a needle component 1618, which may include one or more of the following: a needle hub 1620, the needle 1616, a first grip 1622a, and a second grip 1622b (not illustrated in FIG. 3A). In some embodiments, the first grip 1622a may be disposed on an opposite side of the needle hub 1620 as the second grip 1622b. In some embodiments, the needle hub 1620 may include a distal end 1624, a proximal end 1626, and an actuator button 1628. In some embodiments, the actuator button 1628 may be disposed on a top portion of the needle hub 1620.

In some embodiments, the needle 1616 may extend distally from the needle hub 1620 along an axis 1630. In some embodiments, the wings 1614a, 1614b may be parallel to the axis 1630. In some embodiments, the first grip 1622a and/or the second grip 1622b may be generally parallel to the axis 1630 and/or disposed on a side of the needle hub 1620. In some embodiments, the first grip 1622a and/or the second grip 1622b may extend from the side and/or a bottom of the needle hub 1620. The first grip 1622a and/or the second grip 1622b may be integrally formed with the needle hub 1620 or may be coupled with the needle hub 1620 via any suitable mechanism.

As illustrated in FIG. 3A, in some embodiments, the needle component 1618 may include the first grip 1622a but not the second grip 1622b. In some embodiments, the second grip 1622a may allow the user to reach the hand of the user over the IV catheter system 1600 and cradle both the first grip 1622a and the second grip 1622b in the hand of the user. In some embodiments, the needle hub 1620 may be long enough to enclose the needle 1616, capturing both a proximal and distal end of the needle 1616. Thus, the user may prefer to cradle both the first grip 1622a and the second grip 1622b to better support the length of the needle hub 1620.

In some embodiments, the first wing 1614a may be positioned to receive first contact from the first digit of the hand of the user to urge the catheter hub 1604 distally. The first digit of the hand may include, for example, a thumb of the user. In some embodiments, the first grip 1622a of the needle component may be positioned to receive second contact from the second digit of the hand simultaneously with receipt of the first contact such that the first and second contacts cooperate to move the IV catheter system 1600 from the insertion configuration toward the fluid delivery configuration. The second digit may include, for example, an index finger of the user.

In some embodiments, the first grip 1622a may include an upper surface 1632. In some embodiments, the upper surface 1632 may receive the second contact. In some embodiments, when the IV catheter system 1600 is in the insertion configuration, the upper surface 1632 may be coplanar with an upper surface 1634 of the first wing 1614a of the securement platform 1608. In some embodiments, a distal end of the first grip 1622a may contact a proximal end of the first wing 1614a when the IV catheter system 1600 is in the insertion configuration. In some embodiments, the upper surface 1634 of the first wing 1614a may receive the first contact. In embodiments where the second grip 1622b is present, the second grip 1622b may be configured similarly to the first grip 1622a. Movement of the second grip 1622b with respect to the second wing 1614b may be similar to movement of the first grip 1622a with respect to the first wing 1614a. In some embodiments, the second grip 1622b may be a mirror image of the first grip 1622a.

In some embodiments, the needle hub 1620 may include a first gripping protrusion 1638a and/or a second gripping protrusion 1638b, which may each be disposed proximal to the first grip 1622a and/or the second grip 1622b. In some embodiments, the second gripping protrusion 1638b may be disposed on an opposite side of the needle hub 1620 as the first grip 1622a. In some embodiments, the second gripping protrusion 1638b may be positioned to receive third contact from a third digit of the hand of the user simultaneously with the first contact and the second contact, which may provide additional support and control of the IV catheter device 1600. The third digit may include, for example, a middle or ring finger of the user.

In some embodiments, the actuator button 1628 may be disposed on the top portion of the needle hub 1620, which may facilitate easy access of the actuator button 1628 and prevent blocking of the actuator button 1628 by the first digit and/or the second digit during movement toward the fluid delivery configuration.

Figure 3B:
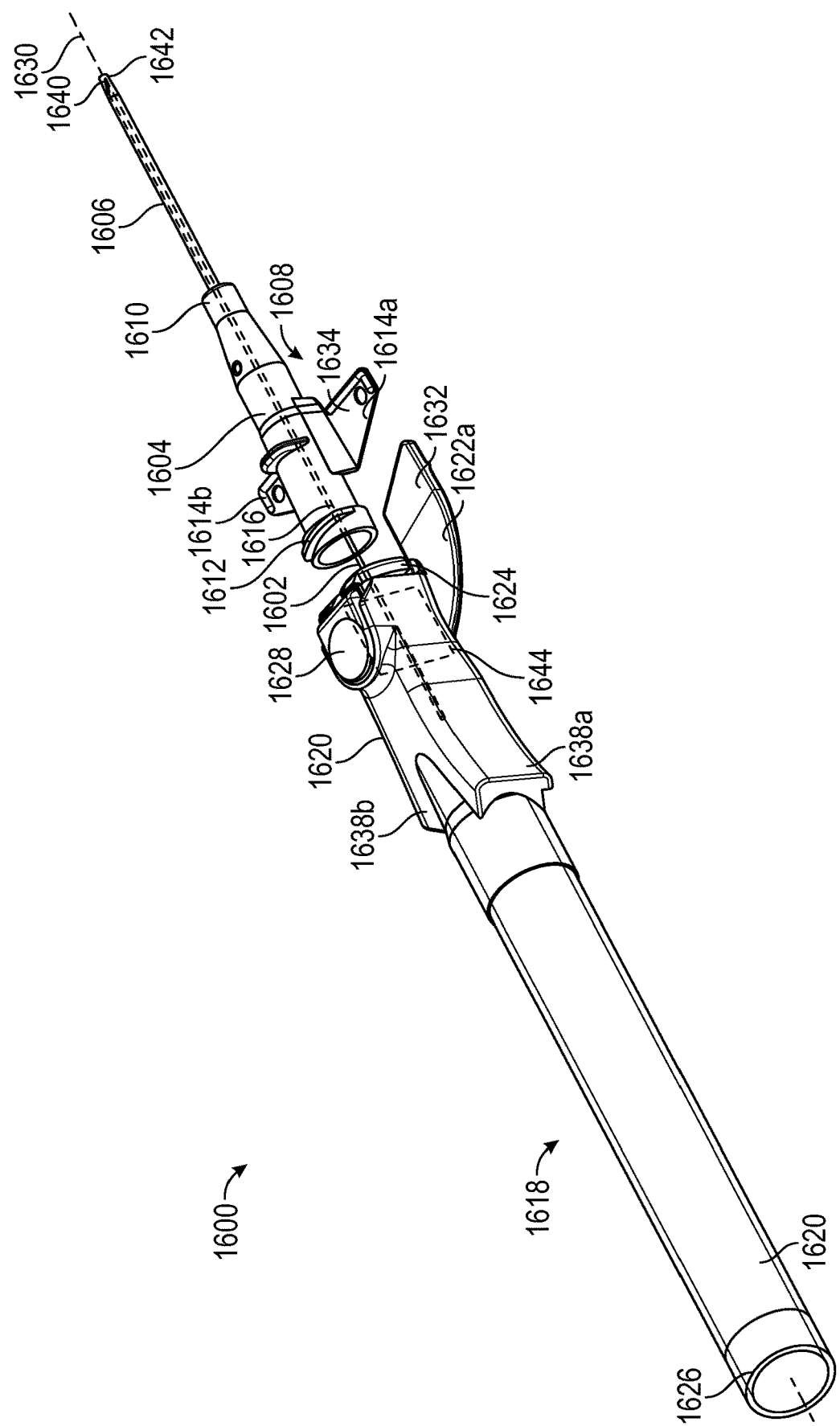
FIG. 3B is a perspective view of the IV catheter system of FIG. 3A, illustrating the IV catheter system moved towards a fluid delivery configuration.

FIG. 3B is a perspective view of the IV catheter system 1600, illustrating the IV catheter system 1600 moved towards the fluid delivery configuration. In some embodiments, when the IV catheter system 1600 is moved towards the fluid delivery configuration, the proximal end of the first wing 1614a and the distal end of the first grip 1622a may be spaced apart. In some embodiments, the IV catheter system 1600 may be inserted and moved toward the fluid delivery configuration with only one hand. Moving the IV catheter system 1600 toward the fluid delivery configuration may facilitate "hooding" of the needle 1616. In some instances, a diameter of a targeted vein may be relatively small compared to a gauge of the needle 1616. Thus, it is not uncommon for a beveled portion 1640 of the needle 1616 to breach or otherwise damage the vein while advancing the cannula 1606 and the needle 1616 into the vein. Accordingly, it is a common practice to "hood" the needle 1616 once the vein has been accessed via the needle 1616 and tip 1642 of the cannula 1606.

A process of hooding the needle 1616 may involve maintaining a stationary position of the partially inserted cannula 1606 while simultaneously withdrawing the beveled portion 1640 of the needle 1616 into the inner lumen of the cannula 1606. Once the needle 1616 has been hooded, the cannula 1606 may be advanced into the vein to a desired position. With the needle 1616 hooded, a danger of damaging the vein may be greatly reduced while advancing the cannula 1606. In some instances, when the needle 1616 is hooded, the beveled portion 1640 may be withdrawn into the inner lumen of the cannula 1606 such that the beveled portion 1640 is at least proximate the tip 1642 of the cannula 1606. Thus, the needle 1616 extending through the cannula 1606 and at least proximate the tip 1642 of the cannula 1606 may provide increased rigidity as the cannula 1606 is advanced into the vein. In some embodiments, the needle 1616 may include a hypodermic needle such as, for example, an introducer needle.

In some embodiments, the actuator button 1628 may be configured to retract the needle 1616 into the needle hub 1620 such that the needle 1616 is entirely enclosed and/or trapped within the needle hub 1620 in the fluid delivery configuration.

In some embodiments, the first wing 1614*a* may be positioned to receive the first contact from the first digit of the hand of the user to urge the catheter hub 1604 distally to a position illustrated in FIG. 3B. The first digit of the hand may include, for example, a thumb of the user. In some embodiments, the first grip 1622*a* of the needle component may be positioned to receive the second contact from the second digit of the hand simultaneously with receipt of the first contact such that the first and second contacts cooperate to move the IV catheter system 1600 from the insertion configuration toward the fluid delivery configuration, hooding the needle 1616, as illustrated in FIG. 3B. The second digit may include, for example, an index finger of the user.

In some embodiments, in response to movement of the IV catheter system 1600 towards the fluid delivery configuration and movement of the catheter hub 1604 distally, a portion of the needle 1616 between the catheter hub 1604 and the needle hub 1620 may be exposed.

The needle 1616 may be retracted into the needle hub 1620 in any number of ways. In some embodiments, a spring 1644 may provide a biasing force for retracting the needle 1616 into the needle hub 1620 when the actuator button 1628 is depressed. FIG. 3B illustrates the spring 1644 in a compressed configuration with significant stored energy.

Figure 3C:
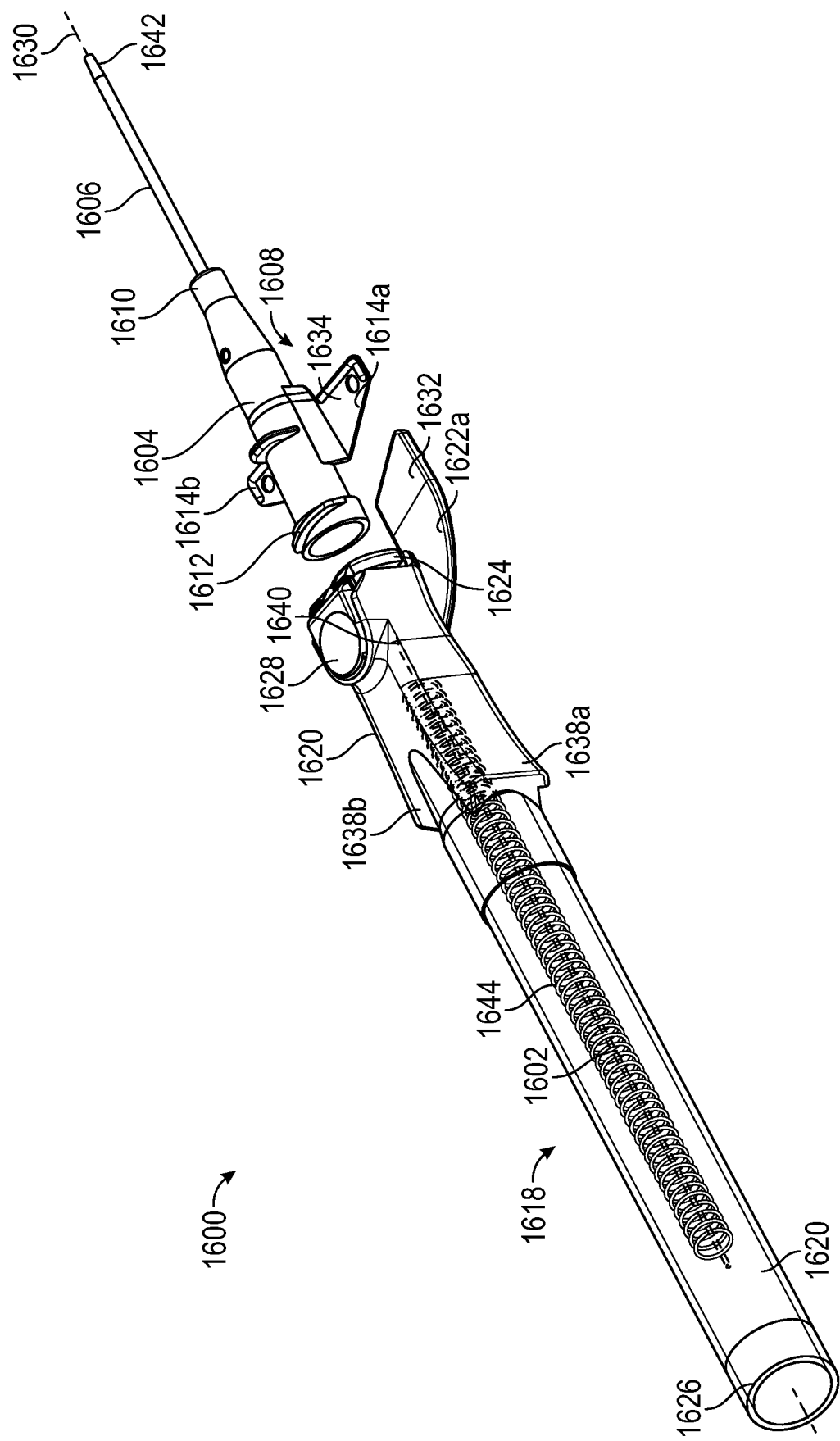
FIG. 3C is a perspective view of the IV catheter system of FIG. 3A, illustrating the IV catheter system in the fluid delivery configuration.

FIG. 3C is a perspective view of the IV catheter system 1600 in the fluid delivery configuration. In some embodiments, once the IV catheter system 1600 is moved toward the fluid delivery configuration to hood the needle 1616 and the cannula 1606 is advanced to the desired position, the actuator button 1628 may be depressed to move the needle 1616 into the needle hub 1620 such that the needle 1616 is entirely enclosed within the needle hub 1620 in the fluid delivery configuration, as illustrated in FIG. 3C. In some embodiments, in the fluid delivery configuration, the spring 1644 may be disposed in a decompressed configuration, having released the stored energy and moved the needle 1616 into the needle hub 1620.

Figure 4A:
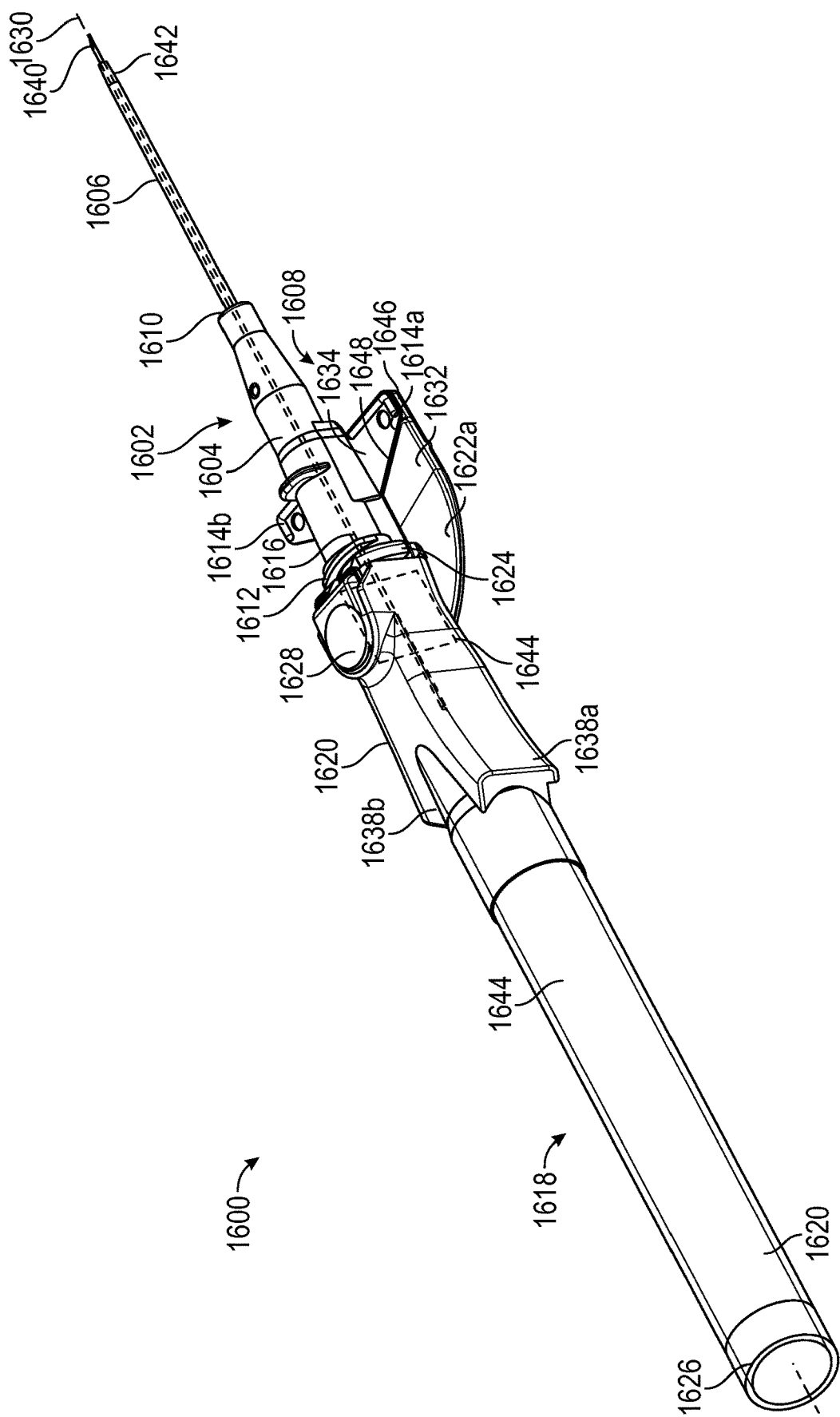
FIG. 4A is a perspective view of an IV catheter system according to yet another embodiment, illustrating the IV catheter system in the insertion configuration.
Figure 4B:
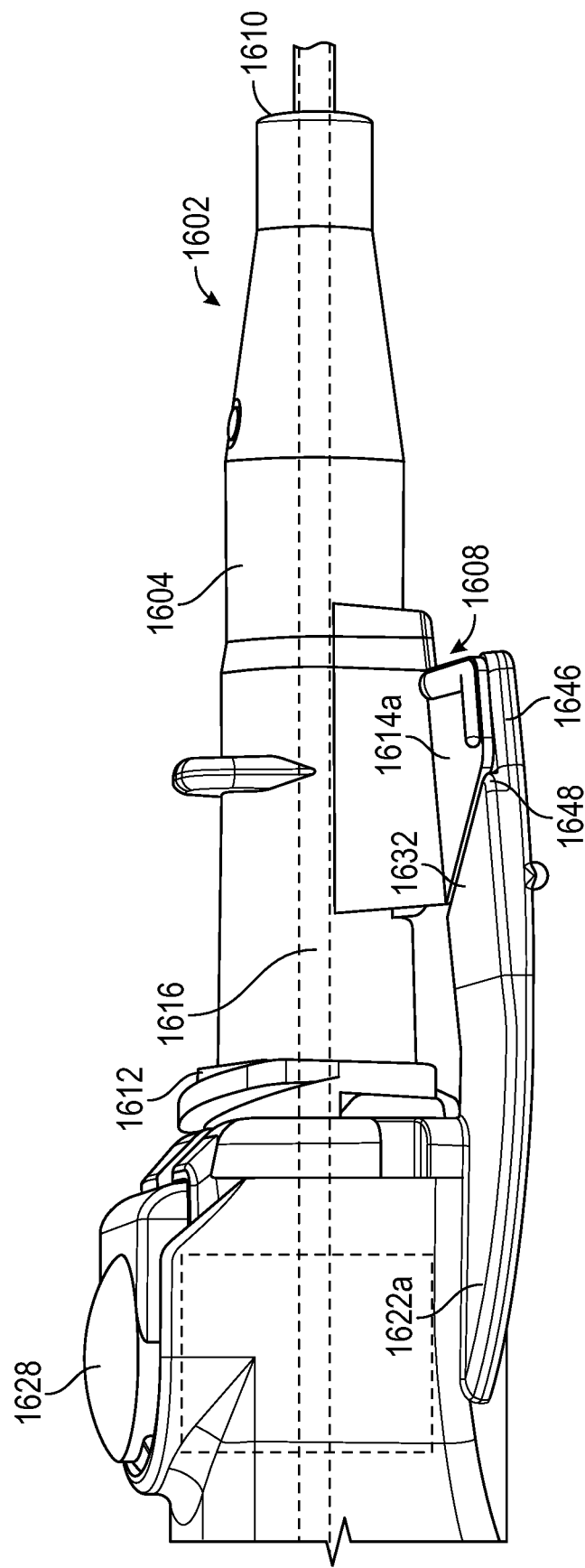
FIG. 4B is a side view of the IV catheter system of FIG. 4A.
Figure 4C:
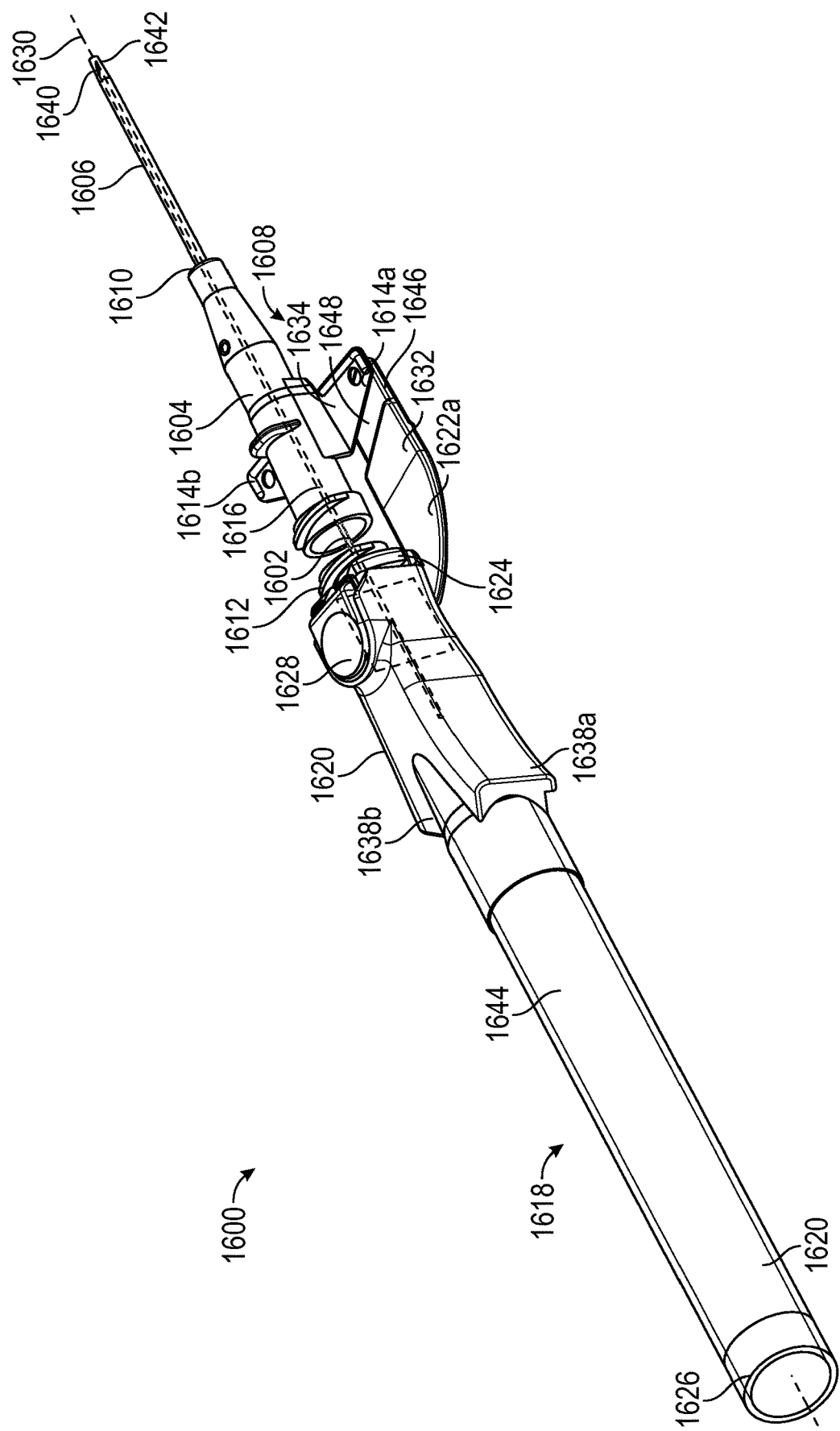
FIG. 4C is a perspective view of the IV catheter system of FIG. 4A, illustrating the IV catheter system moved towards the fluid delivery configuration.
Figure 4D:
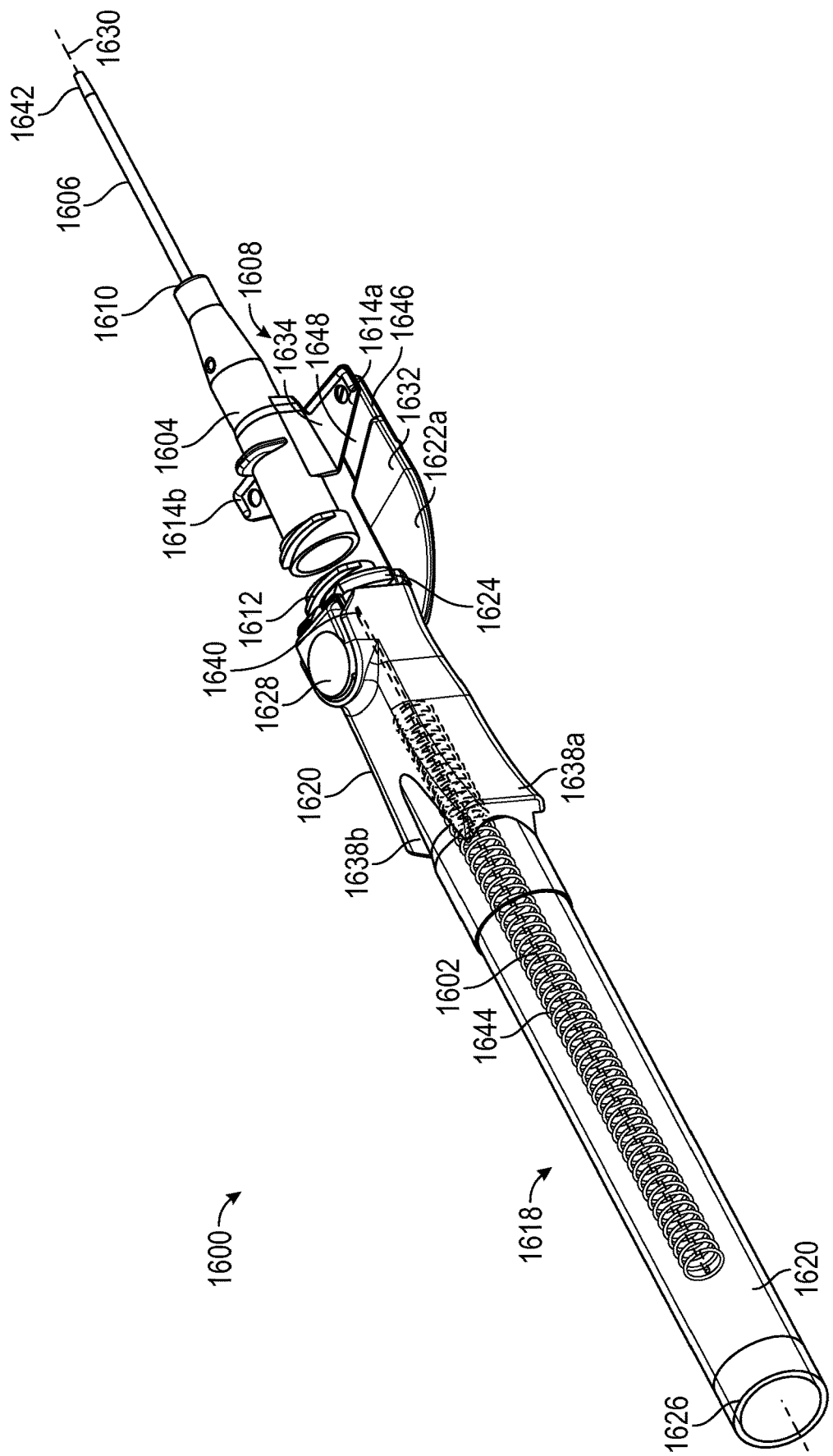
FIG. 4D is a perspective view of the IV catheter system of FIG. 4A, illustrating the IV catheter system moved towards the fluid delivery configuration.

Referring now to FIGS. 4A-4D, in some embodiments, the first grip 1614*a* may include a support surface 1646. In some embodiments, when the IV catheter system 1600 is in the insertion configuration, as illustrated in FIGS. 4A-4B, at least a portion of a bottom surface of the first wing 1614*a* may contact the support surface 1646. For example, an entire bottom surface of the first wing 1614*a* may contact the support surface 1646.

In some embodiments, the first grip 1622*a* may include a stop surface 1648, which may separate the upper surface 1632 of the first grip 1622*a* from the support surface 1646. In some embodiments, when the IV catheter system 1600 is in the insertion configuration, the proximal end of the first wing 1614*a* may contact the stop surface 1648. In some embodiments, the support surface 1646 may extend from the stop surface 1646 to the distal edge of the first wing 1614*a*. In some embodiments, the support surface 1646 may extend only part way from the stop surface 1646 to the distal edge of the first wing 1614*a*.

In some embodiments, during motion of the IV catheter system 1600 from the insertion configuration toward the fluid delivery configuration, at least a portion of the bottom surface of the first wing 1614*a* may slide along the support surface 1646. In some embodiments, when the first wing 1614*a* and the first grip 1622*a* are moved toward the fluid delivery configuration, the first wing 1614*a* and the first grip 1622*a* may or may not be spaced apart depending, for example, on an extent of the hooding of the needle 1616 or how far the needle 1616 is withdraw into the cannula 1606.

Again, in embodiments where the second grip 1622*b* is present, the second grip 1622*b* may be configured similarly to the first grip 1622*a*. Movement of the second grip 1622*b* with respect to the second wing 1614*b* may be similar to movement of the first grip 1622*a* with respect to the first wing 1614*a*. In some embodiments, the second grip 1622*b* may be a mirror image of the first grip 1622*a*.

Figure 5:
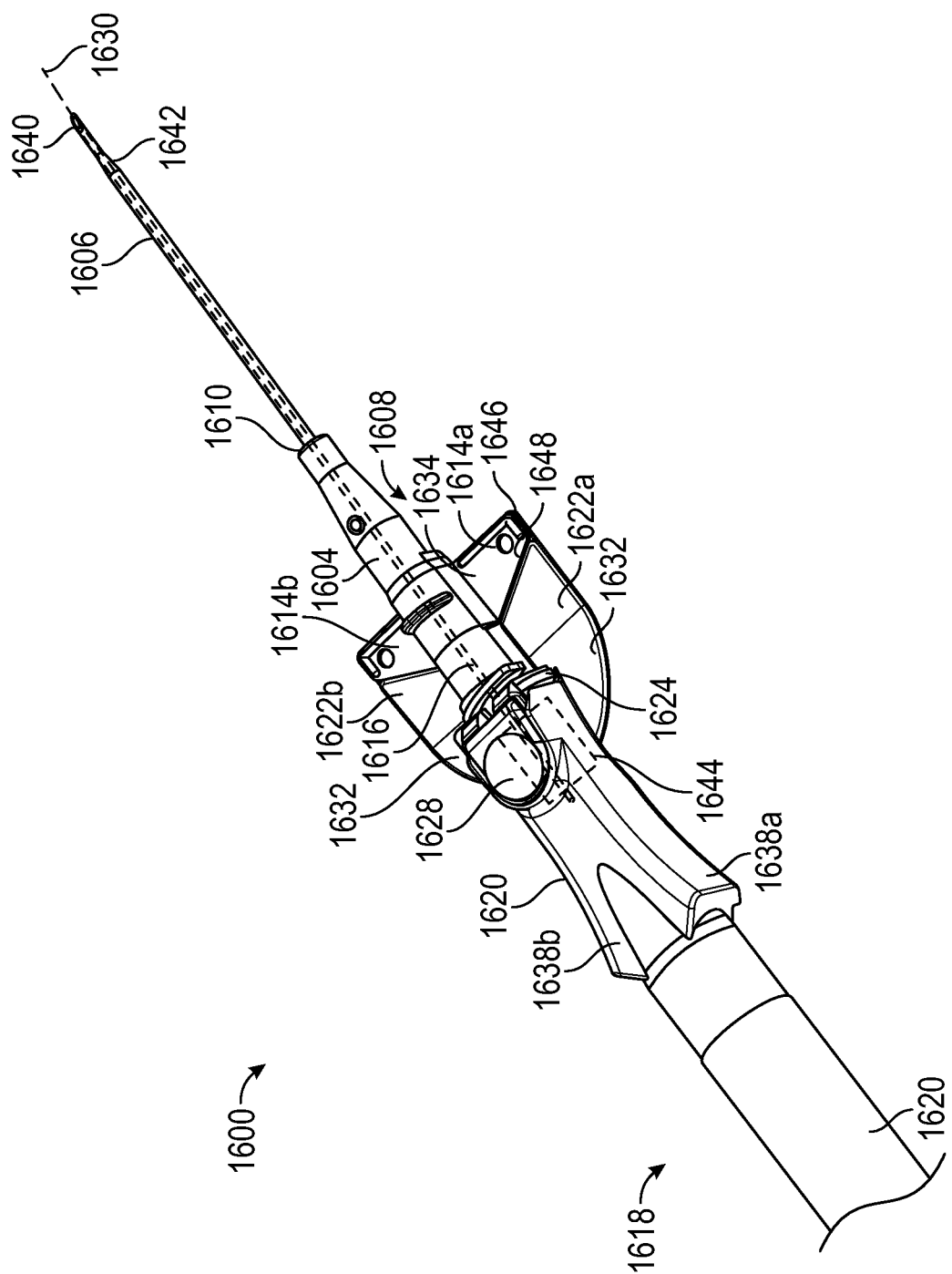
FIG. 5 is a perspective view of an IV catheter system according to yet another embodiment, illustrating the IV catheter system with two grips.

FIG. 5 illustrates the IV catheter system 1600 including the first grip 1622*a* and the second grip 1622*b*. In some embodiments, the IV catheter system 1600 with the first grip 1622*a* and the second grip 1622*b* may include the support surfaces 1646. In other embodiments, the IV catheter system 1600 with the first grip 1622*a* and the second grip 1622*b* may not include the support surfaces 1646. In some embodiments, the actuator button 1628 may be disposed between the first grip 1622*a* and the second grip 1622*b*.

Figure 6:
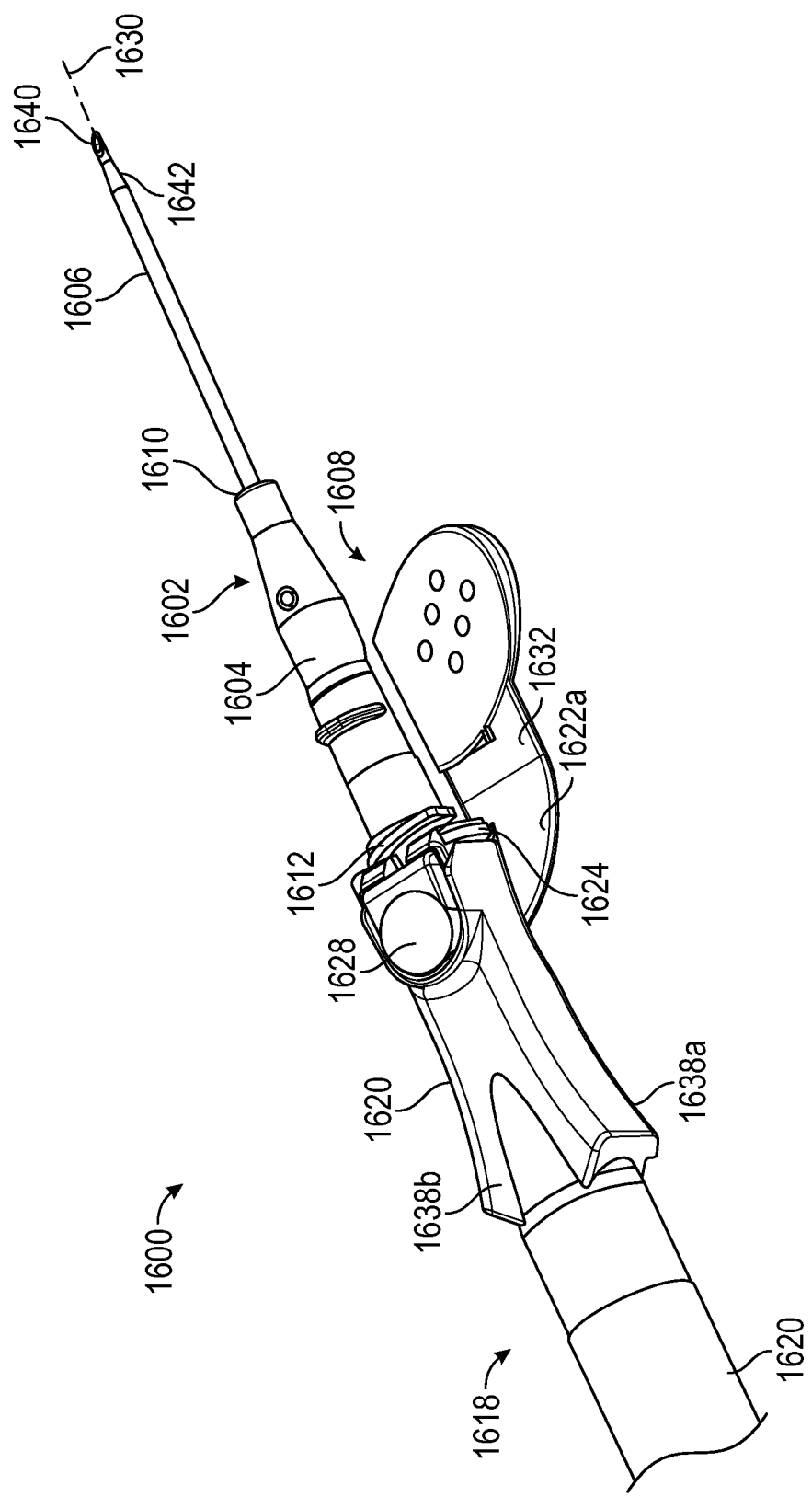
FIG. 6 is a perspective view of an IV catheter system according to yet another embodiment, illustrating the IV catheter system in the insertion configuration.
Figure 7:
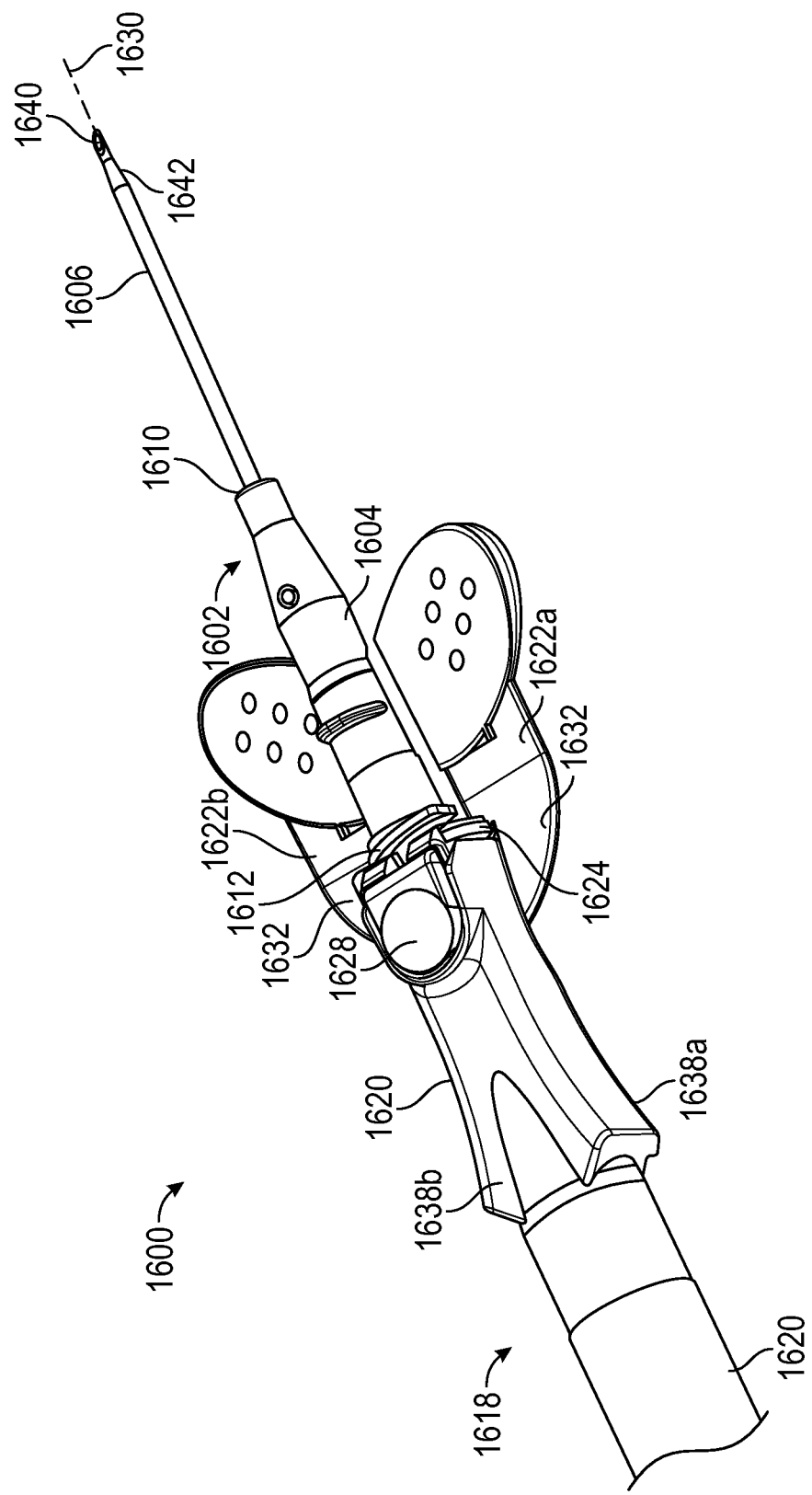
FIG. 7 is a perspective view of an IV catheter system according to yet another embodiment, illustrating the IV catheter system in the insertion configuration.

FIGS. 6-7 illustrate the IV catheter system 1600 according to some embodiments. The IV catheter system 1600 is illustrated in the insertion configuration in FIGS. 6-7. As illustrated in FIGS. 6-7, in some embodiments, the catheter hub 1604 may not include the first wing 1614*a* and/or the second wing 1614*b*. In some embodiments, the grip 1622*a* may extend beyond the distal end 1612 of the catheter hub 1604 and/or may be spaced apart from the catheter hub 1604. In some embodiments, all or a portion of the grip 1622*a* may be generally planar.

In some embodiments, the IV catheter system 1600 illustrated in any or all of FIGS. 3-7 may have components similar to those of the IV catheter systems of previous embodiments. The IV catheter system 1600 illustrated in any of FIGS. 3-7 may include any catheter system that includes a needle retractable into a needle hub. In some embodiments, the IV catheter system 1600 may include the AUTOGUARD™ shielded catheter commercially available from Becton, Dickinson, and Company. Specifically, in some embodiments, the IV catheter system 1600 may include the INSYTE™ AUTOGUARD™ or the ANGIOCATH™ AUTOGUARD™. In some embodiments, the IV catheter system 1600 may include any catheter system that includes a needle movable from a first position when the IV catheter system is in the insertion configuration, to a second position when the needle is hooded and the IV catheter system is transitioning from the insertion configuration to the fluid delivery configuration, and to a third, retracted or enclosed position when the IV catheter system is in the fluid delivery configuration.

The catheter hub 1604 may or may not include a septum, such as, for example, a blood control septum. In some embodiments, once the needle 1616 is retracted, the septum may close, which may prevent blood from flowing proximally beyond the septum. In some embodiments, when a luer connection is made to the IV catheter system 1600, the septum may be opened, allowing flow into the catheter 1606.

In some embodiments, a method for preparing an IV catheter system, such as, for example, the IV catheter 1600, to deliver fluid to a patient, may include positioning the IV catheter system proximate a fluid delivery location of a patient. In some embodiments, the method may also include, with the IV catheter system in the insertion configuration, using a single hand to insert the needle and the cannula into the fluid delivery location. In some embodiments, the method may further include, with the needle and cannula in the insertion configuration, using the single hand to push the wing while pulling the grip to urge the IV catheter system to move from the insertion configuration toward the fluid delivery configuration, in which the needle is positioned outside the catheter hub. In some embodiments, the method may include depressing an actuator button to move the needle into a needle hub of the IV catheter system such that the needle is entirely enclosed within the needle hub in the fluid delivery configuration.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A catheter system, comprising:
   a catheter hub, comprising a distal end and a proximal end;
   a cannula extending distally from the distal end of the catheter hub;
   a needle hub coupled to the proximal end of the catheter hub;
   a needle secured within the needle hub and extending through the cannula;
   a first grip extending outwardly from the needle hub; and
   a second grip opposite the first grip and extending outwardly from the needle hub, wherein the first grip and the second grip extend distal to the proximal end of the catheter hub.

2. The catheter system of claim 1, wherein the first grip and the second grip are spaced apart from the catheter hub.

3. The catheter system of claim 1, wherein at least a portion of the first grip is generally planar and at least a portion of the second grip are generally planar.

4. The catheter system of claim 1, wherein a distal end of the first grip and a distal end of the second grip comprise an oval shape.

5. The catheter system of claim 1, wherein the needle hub comprises an actuator button configured to retract the needle, wherein a proximal end of the first grip and a proximal end of the second grip are aligned with the actuator button.

* * * * *